United States Patent [19]

Alt

[11] Patent Number: 5,928,269
[45] Date of Patent: Jul. 27, 1999

[54] APPARATUS AND METHOD FOR TEMPORARY ATRIAL DEFIBRILLATION WITH EXTERNAL DEFIBRILLATOR AND IMPLANTED TRANSVENOUS CATHETER AND ELECTRODES

[76] Inventor: Eckhard Alt, Eichendorffstrasse 52, Ottobrunn, Germany, 85521

[21] Appl. No.: 08/906,352

[22] Filed: Aug. 5, 1997

Related U.S. Application Data

[63] Continuation-in-part of application No. 08/630,907, Apr. 4, 1996, Pat. No. 5,653,734, which is a continuation of application No. 08/222,242, Apr. 4, 1994, Pat. No. 5,571,159.

[51] Int. Cl.⁶ .................................................. A61N 1/39
[52] U.S. Cl. ........................................................... 607/5
[58] Field of Search ................................. 607/5, 6, 132

[56] References Cited

U.S. PATENT DOCUMENTS 5,403,353   4/1995   Alferness et al. ........................ 607/5

Primary Examiner—William E. Kamm
Attorney, Agent, or Firm—Blank Rome Comisky & McCauley LLP

[57] ABSTRACT

Apparatus is disclosed for temporary treatment of atrial fibrillation of a patient's heart for limited periods of time. An external control unit generates electrical shock impulses; and is electrically connected to spaced-apart defibrillation electrodes of a flexible catheter adapted for temporary implantation in the body of a patient. One of the defibrillation electrodes is positioned in the right atrium of the patient's heart and the other defibrillation electrode is positioned elsewhere proximate the heart to establish a vector through the atrial chambers. A shock impulse is selectively applied from the control unit across the electrodes with a magnitude to establish an adequate field gradient between them so as to cardiovert atrial fibrillation to sinus rhythm. Monitoring of intracardiac and/or surface ECG activity enables detection of the QRS complex to trigger the selective application for delivery of a shock impulse in synchronization with the QRS complex.

18 Claims, 3 Drawing Sheets

APPARATUS AND METHOD FOR TEMPORARY ATRIAL DEFIBRILLATION WITH EXTERNAL DEFIBRILLATOR AND IMPLANTED TRANSVENOUS CATHETER AND ELECTRODES

CROSS REFERENCE TO RELATED APPLICATIONS

This application is a continuation-in-part of application Ser. No. 08/630,907, filed Apr. 4, 1996, now U.S. Pat. No. 5,653,734 which is a continuation of application Ser. No. 08/222,242, filed Apr. 4, 1994, now U.S. Pat. No. 5,571,159 both of which are in the name of the applicant herein, and for which priority is claimed as to common subject matter.

BACKGROUND OF THE INVENTION

The present invention relates generally to treatment of atrial fibrillation, as distinguished from ventricular defibrillation, by discharge of electrical energy in the region of the heart to convert atrial fibrillation into sinus rhythm, and more particularly to temporary monitoring and treatment of atrial rhythm disorders using an external defibrillator in conjunction with a temporary or permanent implanted catheter.

Longer life expectancy has brought with it significantly greater incidence of atrial fibrillation in the industrial nations. Atrial fibrillation is a primary cause of hospitalization for cardiac rhythm disorders in the United States, and an underlying cause of events of cerebrovascular stroke. Proper and timely treatment of atrial fibrillation for conversion to normal sinus rhythm would therefore go far to enhance expectancy and quality of life, and to reduce hemodynamic and thromboembolic complications. The use of anti-arrhythmic drugs has not been highly effective to reduce the incidence of atrial fibrillation, and has had undesirable side effects.

Application of external shocks with energies of between 100 and 350 joules is one therapy for treating atrial fibrillation, but it, too, has a number of risks and complications. Among them are late ventricular fibrillation, pericarditis attributable to the high electrical current, and spinal and other skeletal fractures arising from severe muscular contractions during application of the high energy shock(s).

The art of implanted atrial defibrillation electrodes using lower energies is well developed, as indicated for example by the disclosure of U.S. Pat. No. 5,282,837 dated Feb. 1, 1994 to J. Adams et al. The '837 patent describes the discharge of defibrillating energy from an implanted defibrillator, between two electrodes of an implanted catheter threaded through the coronary sinus. Energy discharge electrodes of the catheter are positioned beneath the left atrium near the left ventricle and in a region adjacent the right atrium coronary sinus ostium to minimize the potential for ventricular fibrillation. The implanted defibrillator senses arrhythmia and controls the energy discharge.

Ventricular fibrillation is also arrested with implanted systems as disclosed by Shulte et al in U.S. Pat. No. 5,269,319. In the '319 patent disclosure, two defibrillation electrodes on a single catheter are inserted via the superior vena cava into the right atrium and right ventricular cavity respectively. R-waves are detected and defibrillation impulse energy is synchronized therewith.

It is a general aim of the present invention to provide improved treatment of atrial fibrillation on a temporary basis, and to correct the deficiencies of the prior art.

A further aim of the invention is to significantly reduce the amount of energy required for treatment of atrial fibrillation from external impulse generators, by means of a hybrid system of internal defibrillating electrodes powered by external energy and control means.

Additional problems exist with necessity to implant prior art electrodes and to deliver sufficient energy for defibrillation. It is questionable whether the installation and operation of an implanted system is worthwhile for treating atrial fibrillation, which occurs only rarely. Effective prior art electrodes have large electrode surface areas to handle the high energy impulses, and are thus generally intrusive when implanted. Also, implantation of netting, barbs and anchors in the region of the heart presents a number of problems for which a solution has not been feasible to address a temporary system.

Conditions such as the potential for congestive heart failure can require continuous monitoring after defibrillation rather than or in addition to mere isolated shock treatment. Furthermore, cardiac surgery may call for post-operative monitoring for atrial dysrhythmias, and the delivery of instantaneous treatment when atrial fibrillation is detected.

Accordingly, it is a further object of the invention to provide a method and associated instrumentation for temporary use for limited periods of time to continuously monitor and instantaneously treat dysrhythmias and atrial fibrillation with adequate electrical field gradient shock energy, and without implantation other than temporarily for a catheter.

SUMMARY OF THE INVENTION

The present invention provides a solution for temporary but on line monitoring and treatment of atrial fibrillation, using methods and apparatus which reduce risk of complications encountered with prior art techniques, and which therefore allow effective treatment of dysrhythmias, and reduced risk of congestive heart failure and post-operative cardiac surgery problems, with relatively little delay.

The invention is directed toward apparatus for temporary treatment of atrial fibrillation of a patient's heart for limited periods of time. The '734 patent discloses a method of treating atrial fibrillation in which there is inserted into the body of the patient a temporary catheter that includes a thin elongate flexible catheter body having a proximal end, a distal end, and a central portion between the proximal end and the distal end. The central portion has a pair of spaced apart low impedance defibrillation electrodes that conform in shape to the central portion to maintain a smooth continuous surface therewith. One of the pair of electrodes is located adjacent the distal end of the catheter. An inflatable balloon is positioned at the distal end, with an inflation lumen of the catheter body running from the proximal end into the balloon. An electrical connector at the proximal end of the catheter connects to a pair of electrical conductors carried by the catheter body to couple the electrical connector to respective ones of the pair of electrodes for selective electrical energization thereof;

The distal end of the catheter body is advanced through the superior vena cava, for example, along a path that includes the right atrium, the right ventricle, and the pulmonary artery adjacent the left atrium of the patient's heart until the distal one of the pair of electrodes is located in a desired position in the pulmonary artery adjacent the left atrium and the other of the electrode pair is located in the right atrium. The balloon is selectively inflated through the inflation lumen to aid maneuvering of the catheter body in advancement along the path, and to temporarily and passively maintain the distal end of the catheter body in the desired position in the pulmonary artery.

When atrial fibrillation is detected and the electrodes are located respectively in the right atrium and in the desired position in the pulmonary artery adjacent the left atrium, the electrode pair is electrically energized with a defibrillating electrical shock of from about three to about seven joules applied from external control and impulse generating equipment via the connector through the electrical conductors, to establish an electric field between the electrodes with a vector through a substantial mass of the right and left atria. The field gradient has a magnitude sufficient to reset the fibrillating atrial cells so as to terminate the atrial fibrillation and convert it to sinus rhythm.

The patient is monitored continuously during high risk periods of time by the external control apparatus for instantaneous treatment of atrial dysrhythmias.

The catheter body includes additional electrodes in its central portion for use in pacing and sensing intracardiac activity of the patient's heart. Cardiac activity is sensed to detect atrial fibrillation and termination thereof, and the heart is paced when necessary to maintain normal sinus rhythm.

The catheter body also includes an additional lumen running from the proximal end to the distal end thereof, through which blood samples may be taken from the patient when the distal end of the catheter body is disposed in the pulmonary artery, to provide additional information concerning the patient's cardiovascular condition. Yet another lumen running from the proximal end to the distal end of the catheter body allows the measurement of pressure in the pulmonary artery.

According to the present invention, the external control and impulse generating equipment (hereinafter referred to as the control apparatus, control box, or control unit) is configured for its location external to the patient's body for generating electrical shock impulses, and is electrically connected to the defibrillation electrode pair of the flexible catheter adapted for temporary implantation in the patient's body. When the catheter is installed, one defibrillation electrode is positioned in the right atrium and the other is positioned elsewhere proximate the heart, preferably in the left pulmonary artery, to establish a vector through the atria. The control unit is adapted for selective application of a shock impulse across the defibrillation electrodes with a magnitude to establish an adequate field gradient between the electrodes to cardiovert atrial fibrillation to normal sinus rhythm. Preferably, the electrical shock impulse is a biphasic pulse wave, and its energy content is adjustable within a range up to approximately 20 joules, optimally between one and ten joules. The monitoring portion of the control unit allows detection of the QRS complex of the patient's ECG to trigger the delivery of a shock impulse across the defibrillation electrodes in synchronization with the QRS complex.

The monitoring equipment includes a display screen for displaying an atrial ECG signal derived from a sensing electrode of the catheter positioned in the right atrium and an intracardiac ECG signal derived from a sensing electrode of the catheter in the right ventricle, along with a surface ECG signal derived from surface electrodes when placed in electrical contact with the patient's body. Further included as part of the monitoring is an indicator that appears on the display screen for displaying correct triggering of each shock impulse relative to the QRS complex so as to avoid false triggering of a shock impulse. A strip chart recorder on the external control unit enables the recording of events before, during and after application of a shock impulse.

For treating other common detected arrhythmias, the control unit stimulus generator supplies stimulating pulses for application to the heart via the pacing electrodes on the temporary catheter.

The invention also resides in a method for temporary treatment of atrial fibrillation of a patient's heart for limited periods of time.

BRIEF DESCRIPTION OF THE DRAWINGS

The above and still further aims, objects features, aspects, and attendant advantages of the invention will become apparent from the following description of the presently contemplated best mode of practicing the invention with reference to a presently preferred embodiment and method thereof, especially when taken in conjunction with the accompanying drawings, in which.

DETAILED DESCRIPTION OF EMBODIMENTS AND METHODS OF THE INVENTION

Common subject matter is disclosed in the applicant's co-pending application Ser. No. 08/630,907, filed Apr. 4, 1996, now U.S. Pat. No. 5,653,734, of which the present application is a continuation-in-part. The '907 application is itself a continuation of application Ser. No. 08/222,242, filed Apr. 4, 1994, now U.S. Pat. No. 5,571,159. The specification of both of the earlier applications is incorporated herein by reference.

Figure 1:
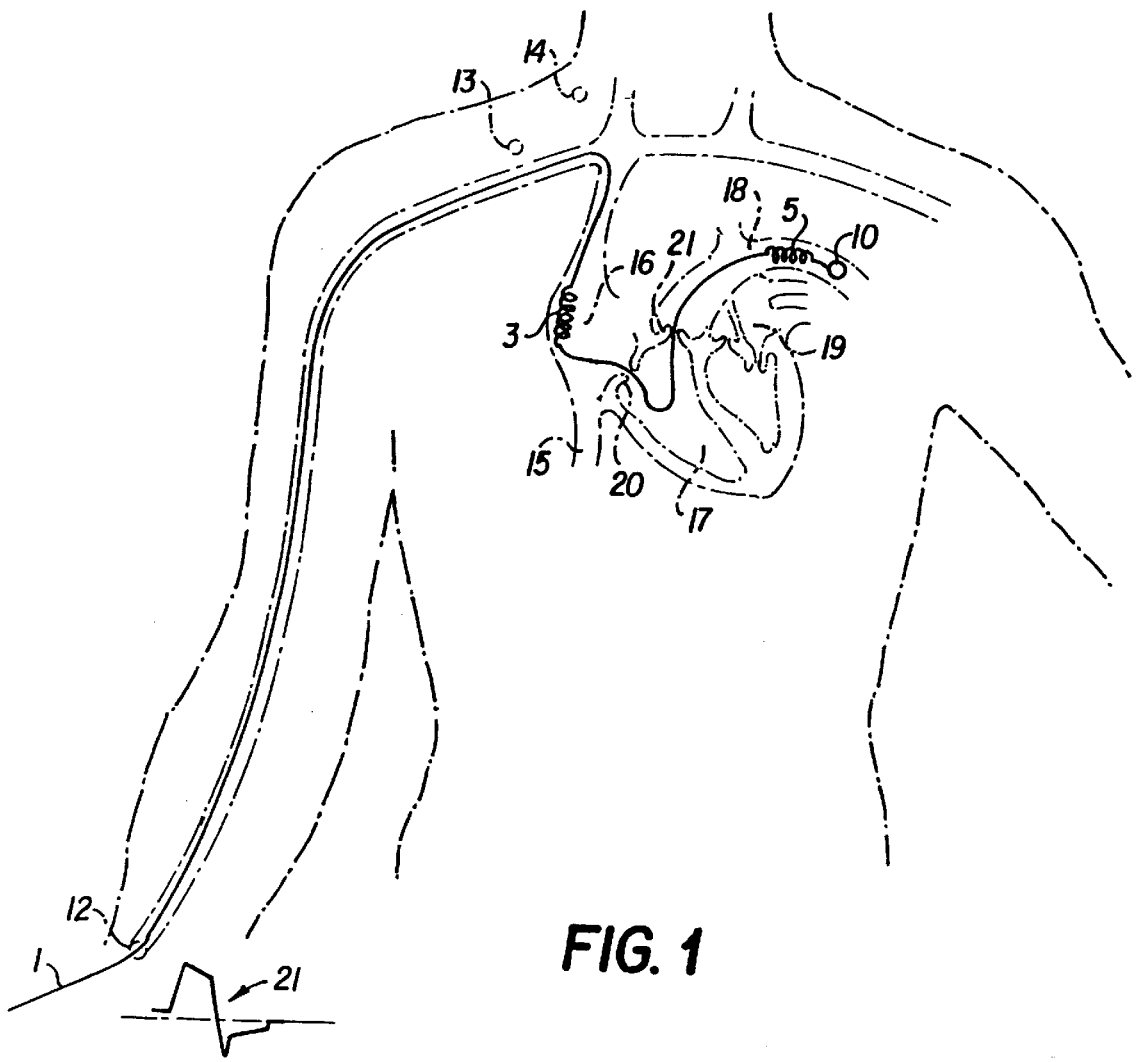
FIG. 1 is an illustration of the placement of the temporary atrial defibrillation catheter in the heart of the patient.

Referring to FIG. 1, a catheter 1 is inserted into the patient's body through a brachial vein puncture site 12 in the right arm and is advanced along the venous system to pass through the superior vena cava and into the right atrium 16 of the heart. The catheter is threaded through a path that includes the right atrium 16, the tricuspid valve 20, the right ventricle 17, the pulmonary valve 21, and finally into the left pulmonary artery 18 adjacent the left atrium 19. Internally embedded conductors 2 and 4 (FIGS. 2, 3) run substantially the length of the catheter from the proximal end where they terminate in connections to an external electrical connector 7 to the distal end where they terminate in electrical connections to defibrillation electrodes 3 and 5 (FIG. 2), respectively. Electrode 5 is located distally of electrode 3, i.e., closer to the distal tip of the catheter. When catheter 1 is fully threaded into position with its distal tip in the left pulmonary artery 18, defibrillation electrode 5 resides in the pulmonary artery and defibrillation electrode 3 resides in the right atrium.

The catheter typically has a diameter of about two millimeters (mm), and is constructed of a polymer sheath to give it sufficiently flexible to pass through the venous system and along the path to its final position shown in FIG. 1. Electrical conductors 2 and 4 are flexible stranded wires suitable for carrying sufficient current called for by the total energy (typically, on the order of three to seven joules) in the shock impulse generated by the external control unit 30 (FIG. 5) to electrodes 3 and 5 to achieve defibrillation. To that end, electrical connector 7 is connected via a mating connector (not shown) to the external control unit for monitoring and instantaneous treatment of atrial dysrhythmias.

Figure 2:
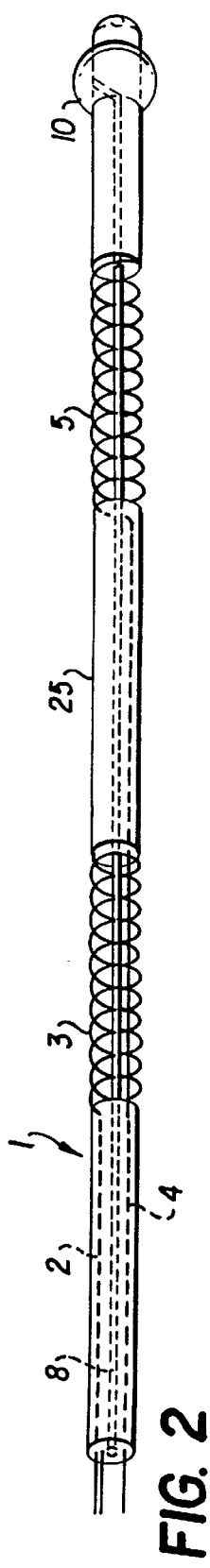
FIG. 2 is a perspective view, partly in section, principally of the distal portion of the catheter and illustrating the defibrillation electrodes.
Figure 3:
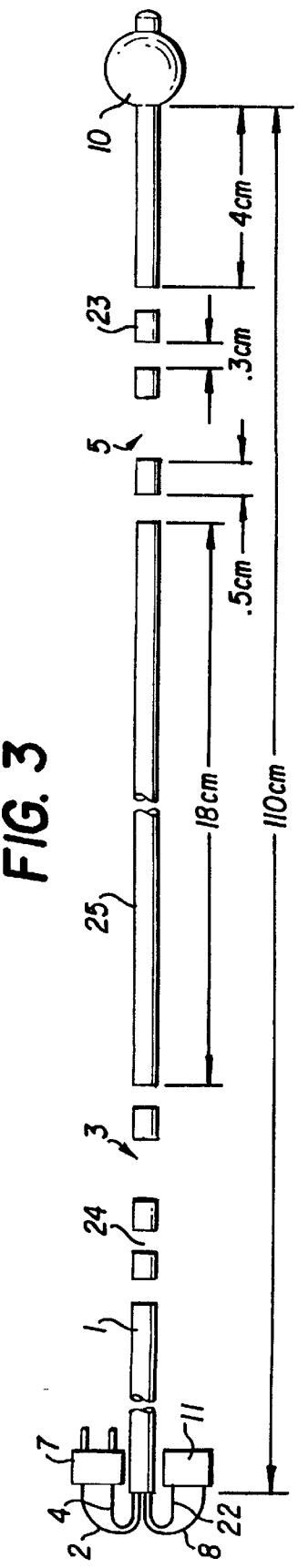
FIG. 3 is a partial side view of the catheter showing certain structural details.
Figure 4:
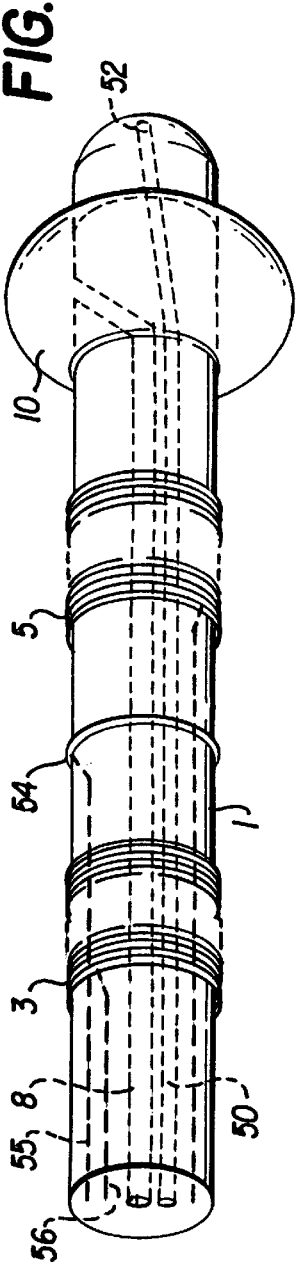
FIG. 4 is a partial perspective view of the distal portion of the catheter illustrating certain lumens therethrough.

The structure of electrodes 3 and 5 is critical for defibrillation, requiring a significant electrode surface exposure area to blood and tissue of the heart for transmitting the necessary shock impulse energy. Preferably, the shock impulse is a biphasic impulse, having a waveform 26 as shown in FIG. 1. To achieve the required surface area and locations for the defibrillation electrodes, they are constructed as shown in FIGS. 2, 3, and 4.

The overall length of catheter 1 is approximately 110 centimeters (cm) and, as previously noted, the outside diameter is typically about two mm. An inflatable balloon 10 is affixed to the distal tip of the catheter and is inflated and deflated through lumen 8 of the catheter which extends from the proximal end at a plug 11 (FIG. 3). The plug provides air control to the balloon by connection to an external syringe of two cc (not shown). Also, for monitoring the blood and the wedge pressure in or near the left pulmonary artery, and for taking blood samples and infusion of fluids to the body, which is particularly critical at the postoperative stage, a further lumen 22 is provided which terminates at or near the distal end of the catheter.

Each of electrodes 3 and 5 is constructed of a series of approximately 0.5 cm long rings 23, typically nine, separated by approximately 0.2 to 0.3 cm spacings 24. The distal electrode 5 is spaced about four cm from the balloon 10, and the two electrodes 3, 5 have an insulating sheath spacer 25 about eighteen cm long between them. The stainless steel rings 23 and interim spacings 24, which constitute insulating catheter sheath polymer material, provide a smooth surface which will not irritate human tissue when passed through the venous system. The area and length of the rings is sufficient to create an electric field gradient of adequate strength through the heart to reset substantially all atrially defibrillating cells and establish sinus rhythm with short duration shock impulse energy of an average of three joules, as confirmed by a study conducted by the applicant in patients with atrial fibrillation following an enlarged and diseased atrium.

The very flexible spacer sheath 25 between the electrodes requires only one electrical wire and is smooth and small diameter so that its position through the pulmonary artery valve 21 for reasonable periods of time will not adversely affect the function of that valve, or of the tricuspid valve 20 through which the catheter also extends. Thus, the catheter may be left in place for several days in a post-operative stage for monitoring and defibrillating in the event atrial fibrillation is detected. Also, the flexible sheath polymer spacers 24 between the stainless steel rings 23 afford enough flexibility at the electrode sites to bend the catheter about body cavities during insertion and positioning of the catheter in the heart. Other types of electrodes such as braided metal mesh would also serve for use as shocking electrodes 3 and 5.

In inserting the catheter, the balloon is initially partly inflated while in the right atrium so as to act as a sail and facilitate the positioning of the catheter by its being carried in the direction of the blood flow through the aforementioned path and into the pulmonary artery, for example. When the distal tip of the catheter reaches the final position in the left pulmonary artery, the balloon is fully inflated from the inflation lumen at the proximal end, to maintain the distal tip in stable position during its temporary placement for treatment. Fixation of the distal tip serves additionally to allow manipulating the shocking electrode 3 into contact with the atrium 16 for good electrical contact when the defibrillation pulse is applied, without danger that the catheter will be dislodged from the anchoring provided at the distal tip. Further, inflation and deflation of the balloon enables measurements of pulmonary wedge pressures.

Alternatively, the catheter may be inserted at the subclavian puncture site 13 or the internal jugular site 14. It would also be possible to approach through the femoral vein and the inferior vena cava 15. In any event, the critical positioning of the catheter and its electrodes shown in FIG. 1 permits a vector of electrical energy to pass through the left atrium 18.

Figure 5:
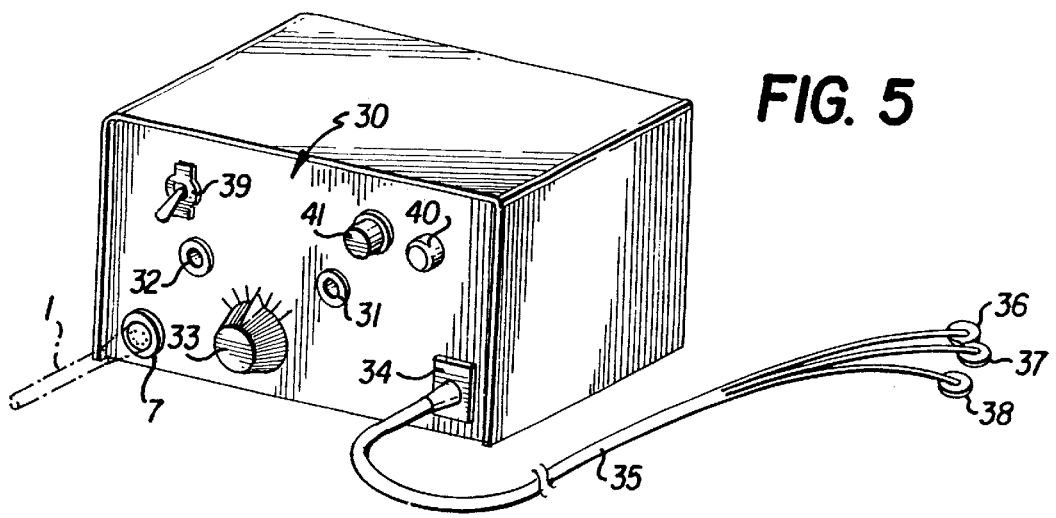
FIG. 5 is a perspective diagram of an embodiment of the external control apparatus of the invention.

The external atrial defibrillator 30 is the control unit shown in FIG. 5. It provides an electrical shock impulse, preferably biphasic (26, FIG. 1) of variable duration, preferably having a first phase pulse of four milliseconds (ms) duration, with a second phase pulse of opposite polarity to that of the first phase pulse and a duration of two and one half ms. The external defibrillator also provides variable energy by appropriate adjustment of knob 33 on the front panel of the defibrillator box, preferably in a range between one and ten joules. Jacks 31 and 32 (or a single electrical connector 7) on the front panel of the box permit the anode and cathode leads 2, 4 of the catheter 1 to be connected to the defibrillator. ECG lead 35 with surface electrodes 36, 37, 38 is used for triggering the defibrillation shock pulse synchronously with the R-wave or the QRS complex. The external defibrillator is turned on and off with switch 39. A temporary mode indicating correct synchronization with the R-wave, or the QRS complex, is indicated by a light-emitting diode (LED) 40 when the momentary switch 41 is depressed for testing without generating shock pulses. Other controls may include atrial fibrillation detectors that can be coupled to automatically generate a shock wave under prescribed conditions, and fluid controls for lumens 8 and 22 to monitor internal body fluids and provide for balloon inflation.

In the depiction of FIG. 4, lumen 50 extends through the catheter to an opening 52 at the distal tip for ingress and egress of blood and body fluids. An additional electrode ring 54 intermediate the defibrillation electrodes 3 and 5 is connected to electrical conductor wire 55 and is arranged on the catheter to be positioned in the right ventricle 17 when the temporary catheter is fully in position, for use in sensing intracardiac ECG activity and pacing the ventricle. Another electrode corresponding to ring 54 together with a separate conductor wire corresponding to 55 to which it is connected may be positioned closer to defibrillation electrode 3 so as to be located in the right atrium 16 when the catheter is fully implanted in the temporary configuration. The additional electrode is used for sensing atrial ECG activity and for pacing the atrial chamber. Preferably both of these sensing/pacing electrodes are arranged and located on the catheter so as to be maneuvered into contact with excitable tissue in the respective chamber. These electrodes together with the defibrillation electrodes may be used alternatively to or in addition to the surface electrodes 36, 37 and 38 to sense the R-wave and the QRS complex for triggering the delivery of a defibrillation shock impulse (biphasic pulse 26) in synchronization with the QRS complex. Proper initiation of the shock is important to avoid inducing ventricular fibrillation, which can occur as a consequence of non-synchronized application of the shock.

Figure 6:
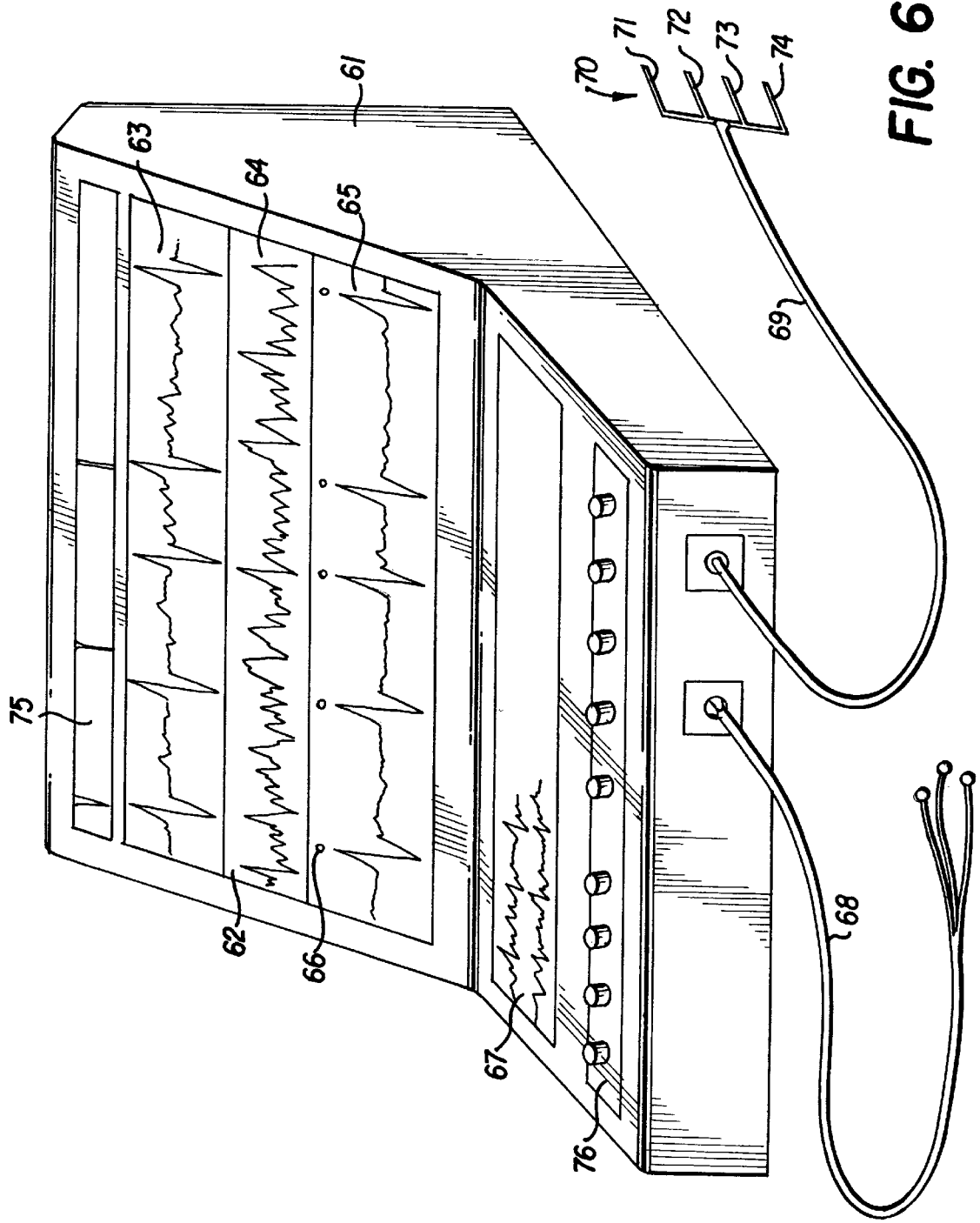
FIG. 6 is a perspective and block diagram of the presently preferred embodiment of the external control apparatus of the invention.

Referring now to FIG. 6, an improved and preferred embodiment of the external atrial defibrillator includes a control unit 61 which includes a monitor, preferably a plasma display screen 62. The surface ECG signal 63 obtained from the surface electrodes when in place on the patient is monitored in one portion of the display, while additional signals representative of atrial activity 64 and the intracardiac ECG activity 65 are displayed on the screen as derived from the atrial and ventricular sensing/pacing electrodes respectively. The display signal 64 is indicative of atrial fibrillation, at the particular time that signal is presented on the screen 62.

The correct triggering of the electrical shocks from the control unit 61 is indicated by dots 66 on the display screen, which indicate that the amplification (and sensitivity) is not too low to preclude reliable detection of the signals and not too high to cause false triggering (false shocking) to take place. Additionally, the control unit 61 has an ECG strip recorder to record on strip 67 the surface ECG signal derived from the surface electrodes of lead 68 when placed in contact with the patient's body. Lead 69 is a schematic representation of the atrial defibrillation catheter (or at leads symbolic of the electrical conductors therein), which is connected by means of an electrical connector to the control unit. Lead 69 has four plug type connections 70. Connection 71 is for the atrial defibrillation electrode (array) 3, connection 72 is for the atrial pacing ring, connection 73 is for the ventricular pacing ring, and connection 74 is for the distal defibrillation electrode 5. Shocks are applied between connections 71 and 74, and triggering is preferably accomplished between 72 and 73 (although other vectors may alternatively be used, if desired).

For tracing 74, the signals are from connections 71 and 72, and for the tracing 75 the signals from connection 73 is displayed relative to the connection 74 for the distal array. Automatic or manually adjustable gain control is used to aid in providing proper triggering, but as an alternative a triggering wire surface electrode of lead 68 may be used.

A control field 75 on the plasma screen operates in a "windows-like" environment, with appropriate knobs and switches on an operating panel 76 of the control unit serving to operate a cursor on the display 75 to enable selection of the appropriate energy sensing and pacing level, and as well for selection of the application of pacing pulses and the triggering of shocking pulses. Operating panel 76 may also be used to control the windows panel 75 for ECG leads, ECG amplification, and ECG control.

It will thus be seen that the present invention provides an external atrial defibrillator for temporary use for limited periods of time to instantaneously treat dysrhythmias and atrial fibrillation of a patient's heart by use of an external control box that generates electrical shocks of sufficient energy for cardioverting atrial fibrillation, as well as stimulating pulses for pacing the patient's heart when required. The control box is electrically connected to the lead which is temporarily inserted in the patient's heart, for delivering the electrical shocks through the atria for the cardioversion. The control unit shock impulse generator is triggered to selectively initiate application of the electrical shocks to the heart lead in synchronism with a designated portion of the patient's ECG, specifically, the QRS complex. The amount of energy delivered in each electrical shock is adjustable within a range from one to 20 joules, and preferably from one to 10 joules.

Although presently preferred embodiments and methods of treatment have been described herein, various modifications may suggest themselves to persons of ordinary skill in the field of the invention from a consideration of the foregoing detailed description, without departing from the spirit and scope of the invention. It is therefore desired that the present invention shall be limited only by the appended claims and by the rules and principles of applicable law.

What is claimed is:

1. Apparatus for temporary treatment of atrial fibrillation of a patient's heart for limited periods of time, comprising control means for generating electrical shock impulses from a location external to the patient's body; a flexible catheter sized and configured for implantation in a predetermined region of the patient's cardiovascular system and having first and second electrodes on the catheter electrically isolated from each other and sized located and configured for positioning, when said catheter is implanted in said predetermined in the right atrium and a location proximate thereto to establish a vector of an electric field through the right and left atria of the patient's heart when said electrodes are so positioned and energized by said control means; said catheter including means for temporarily and passively anchoring said catheter in position in said predetermined region during said temporary treatment of atrial fibrillation; means for electrically connecting said control means to said catheter for interconnection to said first and second electrodes; said control means including means effective when triggered for selectively applying a shock impulse from said control means across said first and second electrodes when interconnected thereto and said electrodes are so positioned to establish a gradient of said electric field between said electrodes and through the atria of sufficient magnitude to cardiovert atrial fibrillation of the patient's heart to sinus rhythm; and said control means further including monitoring means for sensing atrial fibrillation and for detecting the QRS complex of the patient's cardiac activity to trigger said selective applying means for delivery of said shock impulse in synchronization with the detected QRS complex when atrial fibrillation is sensed.

2. The apparatus of claim 1, wherein said catheter includes a first sensing electrode sized, located and configured for positioning in the right atrium and a second sensing electrode sized, located and configured for positioning in the right ventricle of the patient's heart when said catheter is implanted in position in said predetermined region; and said monitoring means includes;

a display screen for displaying an atrial cardiac signal derived from said first sensing electrode and an intracardiac activity signal derived from said second sensing electrode, and surface electrode means for electrical contact with the patient's body to obtain a surface ECG for display on said display screen.

3. The apparatus of claim 2, wherein said monitoring means further includes a strip chart recorder for recording events before, during and after application of a shock impulse.

4. The apparatus of claim 1, wherein said monitoring means further includes indicator means for displaying correct triggering of each shock impulse relative to the QRS complex on the display screen so as to avoid false triggering of a shock impulse.

5. The apparatus of claim 1 wherein said control means is constructed to generate said electrical shock impulses with individual pulse energy content in a range up to approximately 20 joules.

6. The apparatus of claim 1 wherein said control means is constructed to generate said electrical shock impulses each in the form of a biphasic pulse wave.

7. The apparatus of claim 6 wherein said control means includes means for adjusting the pulse energy content of a single aid biphasic pulse wave within a range of up to approximately 20 joules.

8. The apparatus of claim 1 wherein said control means further includes means for pacing the patient's heart by generating stimulating pulses for application to the heart.

9. An external defibrillator for temporary use for limited periods of time to instantaneously treat dysrhythmias and atrial fibrillation of a patient's heart, comprising a control box for generating electrical shocks of variable energy content sufficient for cardioverting atrial fibrillation; lead means including transvenous electrodes for insertion through a portion of the patient's venous system to position at least one of said electrodes endocardially to produce in concert with at least one other of said electrodes a defibrillating electric field vector through the right and left atria of the patient's heart when an electrical shock of sufficient energy content is applied across said at least one and said at least one other of said electrodes, said transvenous electrodes further including an electrode for sensing atrial fibrillation; an electrical connector for connecting said control box to said lead means to deliver said electrical shocks generated by said control box to said at least one and said at least one other of said electrodes, and to deliver a waveform indicative of cardiac activity from said sensing electrode to said control box; said lead means including means for selective passive anchoring thereof in place in said portion of the patient's venous system during said temporary treatment of atrial fibrillation and for release of said anchoring thereafter to allow removal of said lead means from the patient's body; said control box including trigger means responsive to sensed cardiac activity indicative of atrial fibrillation for selectively initiating application of said electrical shocks generated by said control box to said lead means synchronously with a preselected portion of the patient's ECG waveform; and means for adjusting the energy content of each said electrical shock within a range from one to twenty joules.

10. A method for temporary treatment of atrial fibrillation of a patient's heart for limited periods of time, comprising the steps of providing a control unit for selectively generating electrical shock impulses from a location external to the patient's body; implanting a flexible catheter having defibrillation electrodes and sensing electrodes thereon in the patient's cardiovascular system so that the defibrillation electrodes are located respectively in the right atrium and proximate thereto to establish a vector of an electric field through the right and left atria of the patient's heart when said defibrillation electrodes are so located and energized by said control unit, and so that said sensing electrodes are located on the right side of the heart to detect cardiac activity including atrial fibrillation; temporarily and passively anchoring said catheter in position in the patient's cardiovascular system so that said defibrillation and sensing electrodes are maintained in said locations during said temporary treatment of atrial fibrillation; electrically connecting said control unit to said catheter for monitoring cardiac activity and for applying shock impulses to said defibrillation electrodes when atrial fibrillation is detected; triggering said control unit in response to detection of atrial fibrillation to selectively apply a shock impulse therefrom across said defibrillation electrodes and thereby establish a gradient of said electric field between said defibrillation electrodes and through the atria of sufficient magnitude to cardiovert atrial fibrillation of the patient's heart to sinus rhythm; monitoring the patient's cardiac activity to detect the patient's QRS complex and to control said triggering for delivery of each said shock impulse in synchronization with the detected QRS complex when atrial fibrillation is sensed; and releasing the anchoring of said catheter for removal thereof from the patient's body when said temporary treatment of atrial fibrillation is completed.

11. The method of claim 10, wherein implanting said flexible catheter includes positioning one of said sensing electrodes in the right atrium to obtain an atrial ECG signal therefrom and positioning another of said sensing electrodes in the right ventricle to obtain an intracardiac ECG signal therefrom, and wherein said control unit includes a display screen; and further including the steps of placing surface electrodes on the patient's body to obtain a surface ECG signal; and displaying said atrial ECG, said intracardiac ECG and said surface ECG signals on said display screen.

12. The method of claim 11, including the step of indicating on said display screen of the control unit the correct triggering of each shock impulse relative to the QRS complex of said ECG signals so as to avoid false triggering of a shock impulse.

13. The method of claim 11, including the step of connecting a strip chart to said control unit for recording cardiac events before, during and after application of a said shock impulse generated by said control unit.

14. The method of claim 10 including the step of selecting each said electrical shock impulse generated by said control unit to deliver pulse energy in a range up to approximately 20 joules.

15. The method of claim 10 including the step of configuring each said electrical shock impulse generated by said control unit as a biphasic pulse wave.

16. The method of claim 15 including the step of adjusting the energy content of each said biphasic pulse wave within a range of up to approximately 20 joules.

17. The method of claim 10 further including the step of pacing the patient's heart by generating stimulating pulses from the control unit for application to the heart.

18. A method for external control of fibrillation on a temporary basis to instantaneously treat dysrhythmias and atrial fibrillation of a patient's heart, comprising the steps of providing a control box for generating electrical shocks of variable energy content sufficient for cardioverting atrial fibrillation; inserting a lead having transvenous defibrillation and sensing electrodes through a portion of the patient's venous system to position one defibrillation electrode endocardially in the patient's heart and another defibrillation electrode proximate thereto to produce in concert with said one defibrillation electrode an electric field vector through the right and left atria of the patient's heart when an electrical shock of sufficient energy content is applied across said one and said another of said electrodes, and to position a sensing electrode in the right atrium to sense atrial fibrillation; electrically connecting said control box to said lead to deliver said electrical shocks generated by said control box to said defibrillation electrodes, and to deliver a waveform indicative of cardiac activity from said sensing electrode to said control box; selectively and passively anchoring said lead in place in said portion of the patient's venous system during temporary treatment of atrial fibrillation by inflating a balloon located at the distal end of said lead through an inflation lumen of said lead, and releasing said anchoring after said temporary treatment is completed by deflating said balloon through said inflation lumen to allow removal of said lead from the patient's body; triggering the generation of said electrical shocks from said control box in response to sensed cardiac activity indicative of atrial fibrillation, to selectively initiate application of said electrical shocks to said lead synchronously with a preselected portion of the patient's ECG waveform; and adjusting the energy content of each said electrical shock within a range from one to twenty joules for sufficient energy content to cardiovert the atrial fibrillation.

\* \* \* \* \*